United States Patent
Zaid et al.

(10) Patent No.: US 10,772,347 B2
(45) Date of Patent: Sep. 15, 2020

(54) NUTRITIONAL SUPPLEMENT

(71) Applicant: Ankh Life Sciences Limited, Dublin (IE)

(72) Inventors: Gene H. Zaid, Hutchinson, KS (US); Beth Ann Wolf, Hutchinson, KS (US); Larry D. Crow, Hutchinson, KS (US)

(73) Assignee: Ankh Life Sciences Limited, Dublin (IE)

( * ) Notice: Subject to any disclaimer, the term of this patent is extended or adjusted under 35 U.S.C. 154(b) by 0 days.

(21) Appl. No.: 16/115,284

(22) Filed: Aug. 28, 2018

(65) Prior Publication Data

US 2019/0261667 A1 Aug. 29, 2019

Related U.S. Application Data

(60) Provisional application No. 62/634,406, filed on Feb. 23, 2018.

(51) Int. Cl.
| | |
|---|---|
| *A23L 33/105* | (2016.01) |
| *A61K 31/375* | (2006.01) |
| *A61K 31/11* | (2006.01) |
| *A61K 36/8962* | (2006.01) |
| *A61K 36/9066* | (2006.01) |
| *A61K 36/888* | (2006.01) |
| *A61K 31/575* | (2006.01) |

(52) U.S. Cl.
CPC ............ *A23L 33/105* (2016.08); *A61K 31/11* (2013.01); *A61K 31/375* (2013.01); *A61K 31/575* (2013.01); *A61K 36/888* (2013.01); *A61K 36/8962* (2013.01); *A61K 36/9066* (2013.01)

(58) Field of Classification Search
CPC .................................................... A23L 33/105
See application file for complete search history.

(56) References Cited

U.S. PATENT DOCUMENTS

| | | | |
|---|---|---|---|
| 6,596,313 | B2 | 7/2003 | Rosenbloom |
| 8,039,025 | B1 | 10/2011 | Zaid et al. |
| 9,402,834 | B2 | 8/2016 | Zaid et al. |
| 2015/0374624 | A1 | 12/2015 | Ragot et al. |
| 2017/0042867 | A1 | 2/2017 | Zaid et al. |

FOREIGN PATENT DOCUMENTS

| | | | | |
|---|---|---|---|---|
| CH | 684311 | A5 * | 8/1994 | ............ A61K 36/81 |
| CN | 102886014 | A * | 1/2013 | |
| CN | 102886014 | A | 1/2013 | |
| CN | 103394045 | A * | 11/2013 | |
| EP | 1902631 | A2 | 3/2008 | |
| JP | 07304678 | A * | 11/1995 | |
| JP | 2007174910 | A | 7/2007 | |
| KR | 101478253 | B1 | 12/2014 | |
| WO | WO-02087544 | A1 * | 11/2002 | ........... A61K 9/0056 |

OTHER PUBLICATIONS

Krishnaswamy, Kamala. "Indian functional foods: Role in prevention of cancer". Nutrition Reviews; Nov. 1996; 54, 11; ProQuest. S127-S131. (Year: 1996).*
Moloudizargari et al. Pharmacogn Rev. Jul.-Dec. 2013; 7(14): 199-212. (Year: 2013).*
Buch et al. "Interventional role of Haridra (*Curcuma longa* Linn) in cancer". Clinical Cancer Investigation Journal. vol. 1, Issue 2, pp. 45-50. (Year: 2012).*
Dawaul Khatateef from Kaamil-al-Sena'ah, Part II (10th century AD), Central Council for Research in Unani Medicine, 61-65 Institutional Area, Janak Puri, New Delhi-58, 2005 AD. p. 539. Retrieved from Traditional Knowledge Digital Library. (Year: 2005).*
Meyer-Chissick et al. "Wild Edible Plants in Israel Tradition Versus Cultivation" from Medicinal and Aromatic Plants of the Middle-East. Zohara Yaniv, Nativ Dudai, Eds. pp. 18-20. (Year: 2014).*
Yadav et al. "Efficacy of Haridra Kwath Kawal in Management of Acute Tonsillitis". International Journal of Medical and Clinical Research. vol. 3, Issue 8, 2012, pp. -235-241. (Year: 2012).*
Ali-Shtayeh et al. "National List of Medicinal Plants in Palestine—West Bank and Gaza Strip" BERC, 2014, pp. 1-27.
Ben-Arye et al. "Integrative oncology in the Middle East: from traditional herbal knowledge to contemporary cancer care" Annals of Oncology, 2011, vol. 23, pp. 211-221.
Qneibi et al. "Evaluation of taste, total phenols and antioxidant for fresh, roasted, shade dried and boiled leaves of edible Arum palaestinum Bioss" Marmara Pharmaceutical Journal, 2017, vol. 22, pp. 52-58.
International Search Report and Written Opinion in PCT/US19/18880 dated Apr. 15, 2019.

* cited by examiner

*Primary Examiner* — Amy L Clark
(74) *Attorney, Agent, or Firm* — Hovey Williams LLP

(57) ABSTRACT

Nutritional supplements comprising individual quantities of turmeric, *Peganum harmala*, and *Arum palaestinum* are provided, which promote several aspects of human health. Advantageously, the turmeric is present in an amount greater than that of *Peganum harmala* or *Arum palaestinum*, and the supplements may contain additional beneficial ingredients, such as β-sitosterol, vanillin, garlic, and Vitamin C.

14 Claims, 4 Drawing Sheets

NUTRITIONAL SUPPLEMENT

CROSS-REFERENCE TO RELATED APPLICATION

This application claims the benefit of U.S. Provisional Application Ser. No. 62/634,406 filed Feb. 23, 2018, incorporated by reference herein in its entirety.

BACKGROUND OF THE INVENTION

Field of the Invention

The present invention is broadly concerned with high-quality nutritional supplements which have beneficial effects including support for normal blood glucose and cholesterol levels, prostate health, and normal cellular division. More particularly, the invention is concerned with such supplements including respective quantities of turmeric, *Peganum harmala*, and *Arum palaestinum*.

Description of the Prior Art

A variety of plants have been employed in the support and maintenance of human health. For example, plants from the hills and mountains of Israel, Palestine, and the Golan Heights have been used for many years for supporting and maintaining human health. Among these are extracts of *Arum palaestinum* Boiss. See, for example, Said et al. *Ethnopharmacological Survey of Medicinal Herbs in Israel, the Golan Heights and the West Bank Region*. J. Ethnopharmacology. 83 (2002): 251-265.

*Peganum harmala* is a perennial, glabrous plant which grows spontaneously in the Eastern Mediterranean region. The plant is well known in Iran and is widely distributed and used in the support and maintenance of human health. Studies carried out on the chemical compositions of *Peganum harmala* extracts confirm that beta-carboline and quinazoline alkaloids are important compounds of this plant. The plant is one of the most frequently used plants to aide in hypertension and cardiac health worldwide. See, Moloudizargari et al, *Pharmacological and therapeutic effects of Peganum harmala and its main alkaloids*, Pharmacogn Rev. 7(14): pp. 199-212, 2013.

*Curcuma longa* (turmeric) has been used for thousands of years as a spice and medicinal herb. Turmeric includes minor amounts of curcumin, which has shown to provide anti-inflammatory effects and is a strong anti-oxidant. β-sitosterol is a plant sterol which offers a number of health benefits, whether it naturally occurs in foods or as a part of supplements. See, Cooper, *Health Benefits of β-sitosterol*, Livestrong.com, Aug. 14, 2017. Vitamin C and garlic also have well-known health benefits.

Other references include U.S. Pat. Nos. 6,596,313, 8,039,025, and 9,402,834; US Patent Publications Nos. 2015/0374624 and 2017/0042867; Foreign references CN102886014, EP1902631, JP2007174910, and KR101478253; and the following non-patent references: Ali-Shtayeh et al. "National List of Medicinal Plants in Palestine—West Bank and Gaza Strip" *BERC*, 2014, pp 1-27; Ben-Arye et al. "Integrative oncology in the Middle East: from traditional herbal knowledge to contemporary cancer care" *Annals of Oncology*, 2011, Vol. 23, pp 211-221; and Qneibi et al. "Evaluation of taste, total phenols and antioxidant for fresh, roasted, shade dried and boiled leaves of edible *Arum palaestinum* Bioss" *Marmara Pharmaceutical Journal*, 2017, Vol. 22, pp 52-58.

While the aforementioned naturally occurring products have individually shown promise for various aspects of human health, there have heretofore been no attempts to combine these ingredients for the preparation of beneficial nutritional supplements.

SUMMARY OF THE INVENTION

The present invention provides new nutritional supplements comprising individual quantities of turmeric, *Peganum harmala*, and *Arum palaestinum*.

In preferred practice, the turmeric is present in an amount greater than either of the remaining two extracts, and indeed greater than any of the other ingredients of the compositions, e.g., β-sitosterol, vanillin compound(s), garlic, and Vitamin C. For ease of production and administration, the compositions are advantageously in powdered form and may be provided as individual capsules for daily oral administration.

The invention also provides methods of supporting human health by appropriately administering to a person the nutritional supplements hereof. The supplements may be used in support of the promotion of normal blood glucose and cholesterol levels, for the promotion of prostate health, and for supporting normal cellular division.

DETAILED DESCRIPTION OF THE PREFERRED EMBODIMENTS

Figure 1:
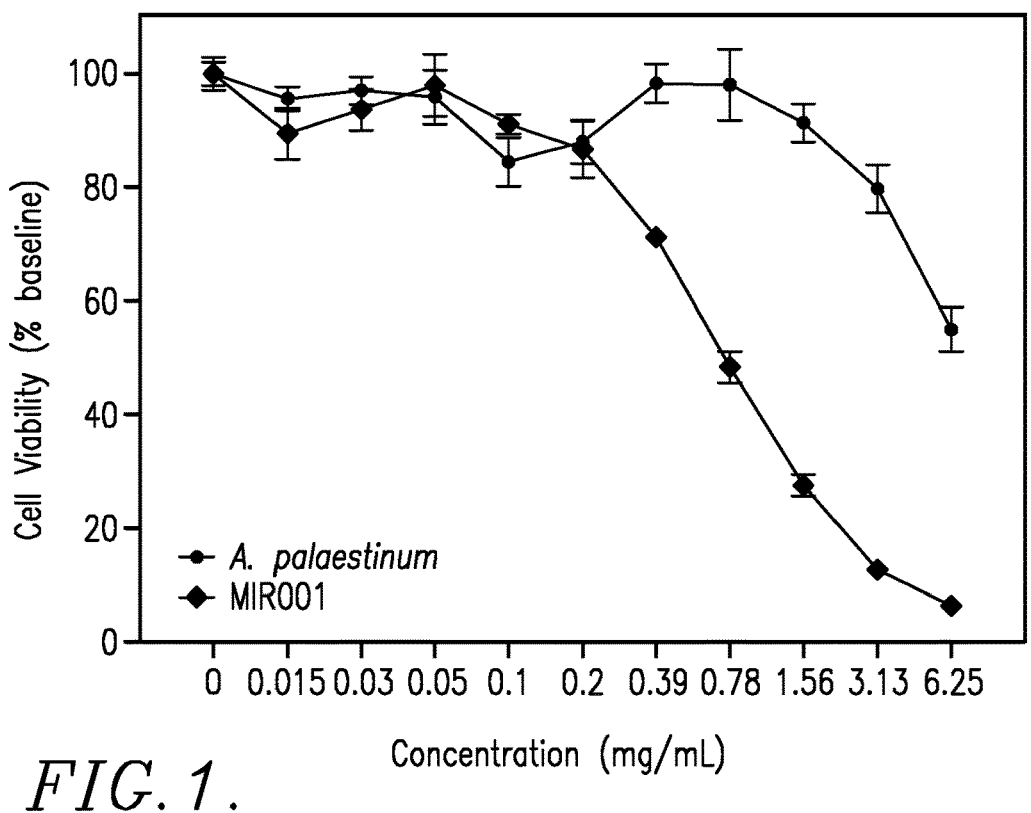
FIG. 1 is a graph illustrating the effect of a three-component plant extract composition (MIR001) made up of *Arum palaestinum*, *Peganum harmala*, and *Curcuma longa* versus *Arum palaestinum* alone on cellular division, as set forth in the Example.

In their broadest aspects, nutritional supplements in accordance with the invention comprise (or consist essentially of, or consist of) individual quantities of turmeric, *Peganum harmala*, and *Arum palaestinum*, as the principal ingredients serving to provide health benefits. In such three-component supplements, the amount of turmeric is greater than either of *Peganum harmala* and *Arum palaestinum*, e.g., such three-component compositions would typically include from about 40-70% turmeric, and from about 15-35% each of *Peganum harmala* and *Arum palaestinum*, based upon the total weight of the three-component supplements taken as 100% by weight. More preferred supplements include these three ingredients together with β-sitosterol, garlic, and Vitamin C, and again the amount of turmeric is preferably greater than any of these other ingredients. For example, such six-component compositions would typically include from about 15-25% turmeric, from about 5-15% each of *Peganum harmala, Arum palaestinum*, β-sitosterol, and garlic, and from about 8-20% Vitamin C. All of the foregoing percentages are by weight, based upon the total weight of the supplements taken as 100% by weight. The supplements may also include significant amounts of vanillin compound(s), such as one or more of vanillin, vanilla, isovanillin, orthovanillin, and ethyl vanillin, which would correspondingly reduce the amounts of the other ingredients therein.

Additional ingredients may be included in the production of complete nutritional supplements. Thus, the supplements may improve other active agents, preservatives, buffering agents, salts, carriers, excipients, diluents, or other ingredients.

Some or all of the ingredients can be in the form of acceptable esters or salts. The esters and salts should be generally safe, non-toxic, and neither biologically nor otherwise undesirable and are acceptable for human use, and which possess the desired degree of activity. Accordingly, the recitation herein of the ingredients of the supplements of the invention is intended to embrace not only the named ingredients, but also any acceptable esters or salts thereof.

Exemplary acceptable salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. The acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is acceptable. Additional examples of acceptable salts and their methods of preparation and use are presented in *Handbook of Pharmaceutical Salts Properties, and Use*, P. H. Stahl & C. G. Wermuth eds., ISBN 978-3-90639-058-1 (2008).

In terms of amounts, the supplements should contain from about 8-15% (more preferably from about 9-11%) Vitamin C, from about 5-11% (more preferably from about 7-9%) garlic, from about 35-45% (more preferably from about 38-42%) vanillin compound(s), from about 5-11% (more preferably from about 7-9%) β-sitosterol, from about 12-20% (more preferably from about 14-17) turmeric, from about 5-11% (more preferably from about 7-9%) *Peganum harmala*, and from about 5-11% (more preferably from about 7-9%) *Arum palaestinum*, where all percentages are by weight, based upon the total weight of the supplements taken as 100% by weight.

Advantageously, all of the ingredients are at least food grade and are blended together as powders. The *Peganum harmala* and *Arum palaestinum* powders may be obtained by drying and pulverizing the complete plants, including leaves, stems, and bulbs; it is not essential that all of the plant parts be used, i.e., use may be made of the leaves, and/or stems, and/or bulbs. The blended powders should be of a size to pass through a 50-mesh screen while being retained by a 100-mesh screen. Still further, the blended powders are placed in capsules for ease of dosage. The capsules should each contain from about 500-1500 mg of the blended powders, most preferably 1000 mg. While such powdered formulations are preferred for ease of manufacture and administration, it should be understood that the invention is not so limited. For example, the blended ingredients may be prepared as liquid dispersions or solutions using appropriate, non-interfering dispersants or solvents; other possible dosage forms include gels, suspensions, or solids such as tablets or pills.

The supplements of the invention, in whatever physical form, are designed for administration to humans, in particularly those seeking to promote or support normal blood glucose levels, normal cholesterol levels, prostate health, and normal cellular division. The supplements may be administered in any convenient manner, such as by oral, rectal, nasal, ophthalmic, parenteral (including intraperitoneal, gastrointestinal, intrathecal, intravenous, cutaneous (e.g., dermal patch), subcutaneous (e.g., injection or implant), or intramuscular) routes. Where the aforementioned capsules are used, the administration would be oral, and the recommended dosage level would be four such capsules per day, taken twice daily, two capsules per serving.

Additional advantages of the various embodiments of the invention will be apparent to those skilled in the art upon review of the disclosure herein. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

In the following examples, a product referred to as "Afaya Plus" was administered to several individuals. Afaya Plus was in the form of capsules, with each capsule containing the preferred ingredients prepared in the ratios outlined above.

Person 1

Person 1 began taking Afaya Plus, 4 capsules daily (2 in the am and 2 in the pm). Baseline blood work was drawn before starting Afaya Plus. After 1 month of administration, Person 1's total cholesterol dropped 11 mg/dL (210 to 199)

and the LDL dropped 7 mg/dL (135-128). This occurred while the person did not report any change in lifestyle, diet, or exercise regimen.

Person 2

Person 2 began taking Afaya Plus, 2 capsules daily (1 in the am and 1 in the pm). Baseline blood work was drawn before starting Afaya Plus. After 1 month of administration, Person 2's total cholesterol dropped 34 mg/dL (247 to 213) and the LDL dropped 31 mg/dL (167 to 136). This occurred while the person did not report any change in lifestyle, diet, or exercise regimen.

Person 3

Person 3 began taking Afaya Plus, 2 capsules daily (1 in the am and 1 in the pm). Baseline blood work was drawn before starting Afaya Plus. After 5 months of administration Person 3's PSA dropped 0.7 ng/mL (1.2 to 0.5), A1C dropped 0.3% (6.1 to 5.8), total cholesterol dropped 19 mg/dL (141 to 122), LDL dropped 4 mg/dL (79 to 75; this occurred after the person was already on high dose statin therapy) and Triglycerides dropped 41 mg/dL (123 to 82). This occurred while the person did not report any change in lifestyle, diet, or exercise regimen.

Person 4

Person 4 began taking Afaya Plus, 2 capsules daily (1 in the am and 1 in the pm). Baseline blood work was drawn before starting Afaya Plus. After 1 month of administration Person 4's A1C dropped 0.2% (5.5 to 5.3) and triglycerides dropped 87 mg/dL (251 to 164). This occurred while the person did not report any change in lifestyle, diet, or exercise regimen.

Person 5

Person 5 began taking Afaya Plus, 2 capsules daily (1 in the am and 1 in the pm). Baseline blood work was drawn before starting Afaya Plus. After 1 year of administration Person 5's PSA dropped 0.28 ng/mL or (0.63 to 0.35). Fasting glucose measurements have trended down over a 1-year period pulled every 3 months (114, 119, 101, 95 mg/dL respectively).

Person 6

Person 6 began taking Afaya Plus, 2 capsules daily (administration times unknown). Person 6's PSA dropped 2.87 ng/mL (3.37 to 0.500) over a period of 15 months of administration (3.37, 1.87, 0.95, 0.72, 0.500 ng/mL respectively).

Person 7

Person 7 began taking Afaya Plus, 2 capsules daily (administration times unknown). Person 7's A1C dropped 0.2% (6.1 to 5.9) over a 6-month period. Person 7 has also reported a downward trend in his 2 hour post prandial sugar levels.

Person 8

Person 8 began taking Afaya Plus, 2 capsules daily (administration times unknown). Person 8's A1C dropped 0.6% (5.8 to 5.2) over a 4-month period. Person 8 has since discontinued taking metformin.

Person 9

Person 9 began taking Afaya Plus (dosage level unknown). Person 9's PSA dropped 1.41 ng/mL (7.1 to 5.69) after 3 months of administration. Person 9's A1C dropped 0.4% (6.5 to 6.1) after 6 months of administration.

Person 10

Person 10 began taking 6 capsules per day—lowered Total Cholesterol from 188 to 151; LDL from 115 to 87; fasting glucose from 106 to 98 in 1 month.

Person 11

Person 11 began taking 2 capsules per day—Lowered Total Cholesterol from 157 to 134 in 1 month; LDL from 86 to 70 in 1 month; A1C from 5.7 to 5.3 over 1 year (TM began taking steroids during this time); PSA lowered from 0.63 to 0.35 over 9 months.

Person 12

Person 12 began taking 4 capsules per day—Lowered Total Cholesterol from 223 to 203 in 1 month; LDL from 140 to 117 in 2 months.

Person 13

Person 13 began taking 4 capsules per day—lowered Total Cholesterol from 214 to 207 in 1 month; LDL from 137 to 124 in 1 month; lowered fasting glucose from 95 to 85 in 1 month Person 14

Person 14 began taking 4 capsules per day—lowered Total Cholesterol from 218 to 197 in 2 months; lowered A1C from 5.5 to 4.9 in 4 months; PSA lowered 7.2 to 1.9 in 3 months Person 15

Person 15 began taking 4 capsules per day—lowered Total Cholesterol from 152 to 134 in 2 months; LDL from 95 to 80 in 2 months Person 16

Person 16 began taking 4 capsules per day—lowered A1C from 8.0 to 6.6 in 5 months Person 17

Person 17 began taking 4 capsules per day—lowered Total Cholesterol from 217 to 169 in 1 month; LDL from 147 to 94 in 1 month;

Person 18

Person 18 began taking 2 capsules per day—lowered Total Cholesterol from 151 to 134 in 2 months; LDL from 97 to 71 in 2 months; fasting glucose from 80 to 66 in 2 months Person 19

Person 19 began taking 2 capsules per day—lowered A1C from 6.0 to 5.3 in 7 months Person 20

Person 20 began taking 2 capsules per day—Lowered fasting glucose from 112 to 87 in 2 months Person 21

Person 21 began taking 2 capsules per day—lowered Total Cholesterol from 173 to 162 in 2 months; LDL from 107 to 92 in 2 months; lowered fasting glucose from 92 to 78 in 1 month Person 22

Person 22 began taking 2 capsules per day—lowered Total Cholesterol from 200 to 182 in 2 months; lowered LDL from 143 to 123 in 2 months; lowered fasting glucose from 128 to 96 in 2 months Person 23

Person 23 began taking 2 capsules per day—lowered fasting glucose from 98 to 84 in 2 months Person 24

Person 24 began taking 2 capsules per day—Lowered Total Cholesterol from 191 to 183 in 1 month; LDL from 98 to 83 in 1 month Person 25

Person 25 began taking 2 capsules per day—lowered Total Cholesterol from 291 to 257 in 1 month; LDL from 180 to 165 in 1 month;

Person 26

Person 26 began taking 2 capsules per day—Lowered Total Cholesterol from 232 to 213 in 1 month; LDL from 160 to 146 in 1 month Person 27

Person 27 began taking 1 capsule per day—lowered Total Cholesterol from 208 to 190 in 1 month; LDL from 102 to 87 in 1 month; fasting glucose from 93 to 82 in 2 months Person 28

Person 29 began taking 1 capsule per day—lowered fasting glucose from 184 to 99 in 2 months Person 29

Person 29 began taking 4 capsules per day lowered PSA from 2.9 to 2.0 in 3 months; lowered fasting glucose from 111 to 93 in 3 months Person 30

Person 30 began taking 2 capsules per day—lowered Total Cholesterol from 257 to 233 in 1 month Person 31

Person 31 began taking 4 capsules per day—lowered LDL from 131 to 107 in 1 month Person 32

Person 32 began taking 2 capsules per day—Lowered Total Cholesterol from 146 to 129 in 3 months; LDL from 84 to 65 in 3 months Person 33

Person 33 began taking 4 capsules per day lowered PSA from 433.8 to 5.5 in 7 months; lowered A1C from 7.6 to 6.4 in 7 months Person 34

Person 34 began taking 2 capsules per day. Blood glucose levels were taken, and illustrated a trend toward lowering of such levels over a period of 210 days, at both morning and two-hour post-prandial (PM) times.

Person 35

Person 35 began taking 4 capsules per day, had to decrease to 3 capsules per day because of glucose levels getting to low. Blood glucose levels were taken, and illustrated a trend toward lowering of such levels over a period of 210 days, at both morning and two-hour post-prandial (PM) times. This Person also had to lower the amount of supplement taken to prevent glucose levels from getting too low. This occurred around day 180.

EXAMPLE

In this example, a set of tests were carried out to compare the effects of the three principal plant extracts used in the invention, alone and in combination, on 3D spheroids from two cancers, namely ovarian and lung cancer.

Materials and Methods.

*Arum palaestinum* Boiss were identified morphologically during field collection from growing habitats in the Palestinian region, and seeds from the plants were then planted in a growth chamber for germination (samples are on file at the Missouri Botanical Garden (MBG) for verification, voucher # Croat 95,466 (MO)). The plant extract was analyzed using gas chromatography-mass spectrometry (GC-MS) to verify identification of *A. palaestinum*. Portions of the plants were cut into wedges and boiled in water for 4 hours, whereupon the wedges were dried to completion in an 80° C. oven. *Peganum harmala* seeds and powdered *Curcuma longa* (turmeric) root were purchased from commercial sources.

A combined product made up of all three of the plant sources (MIR001) were prepared by mixing the powdered extracts at a ratio of 50% by weight turmeric, and 25% by weight each of the *A. palaestinum* and *P. harmala*, followed by boiling for 3 hours. Aliquots were stored at −20° C., and thawed 30 minutes prior to testing in a 37° C. water bath. The thawed aliquots were then vortexed thoroughly and diluted to 6% and 3% concentrations in RPMI with 10% FBS growth media. The individual components of MIR001 were similarly prepared by boiling, freezing, thawing, diluting, and with the addition of RPMI and FBS to create comparative samples.

Human lung cells and human ovarian cells were grown in RPMI 1640 and supplemented with 10% fetal bovine serum and 1% penicillin/streptomycin. In order to form 3D cell clusters, cells were seeded into micromolds at the time of passage. The micromold process has been described previously, Ramachandran K, et al. *Engineering Islets for Improved Performance by Optimized Reaggregation in a Micromold*. Tissue Eng Part A. 2013; 19(5-6):604-12. The process enhances cell aggregation but restricts the aggregates to less than 100 μm in diameter. Cells were grown in the micromolds for 48 hours at 37° C. and 5% $CO_2$, resulting in the formation of uniform 3D spheroids. The 3D models were removed from the micromolds with gentle pipetting and rinsing followed by media change in RPMI with reduced FBS (0.5%). Approximately 25-50 spheroids were distributed per well of a 96 well plate for experimentation.

3D spheroids were seeded and immediately checked microscopically for consistency of cluster distribution between wells. Both cell lines were exposed to multiple replicates of increasing doses of MIR001. Each assay was conducted on a 96 well plate, including 4-6 replicates. In like manner, the individual extracts of MIR001 were tested, along with the RPMI/FBS vehicle.

The MIR001 and extract stock solutions were diluted in RPMI with 10% FBS to reach final desired concentrations. In each experiment, spheroids were exposed to the test article for 24 hours, followed by exposure to 10% PrestoBlue cell viability reagent (Invitrogen) before being loaded into the Enspire microplate reader (Perkin Elmer), with excitation at 490 nm and emission at 560 nm. Background values, obtained from media plus supplement only, were subtracted from each well. For comparisons, changes in PrestoBlue values were normalized to the 0 supplement condition.

Results

Figure 2:
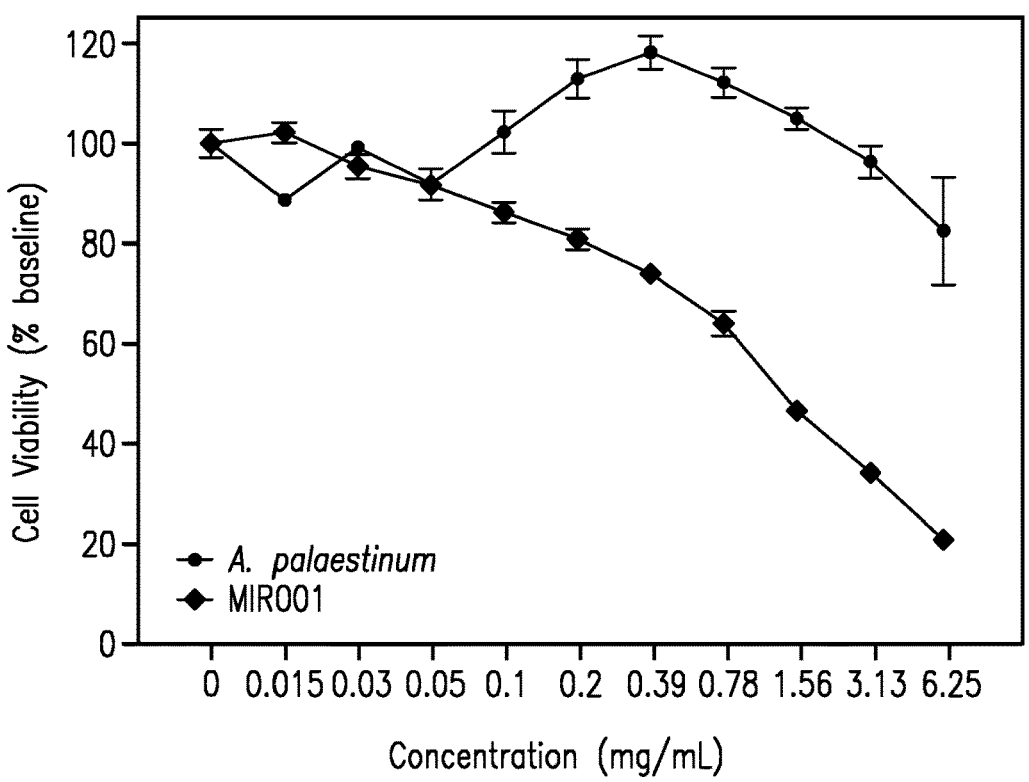
FIG. 2 is a graph illustrating the effect of MIR001 versus *Arum palaestinum* alone, as set forth in the Example.
Figure 3:
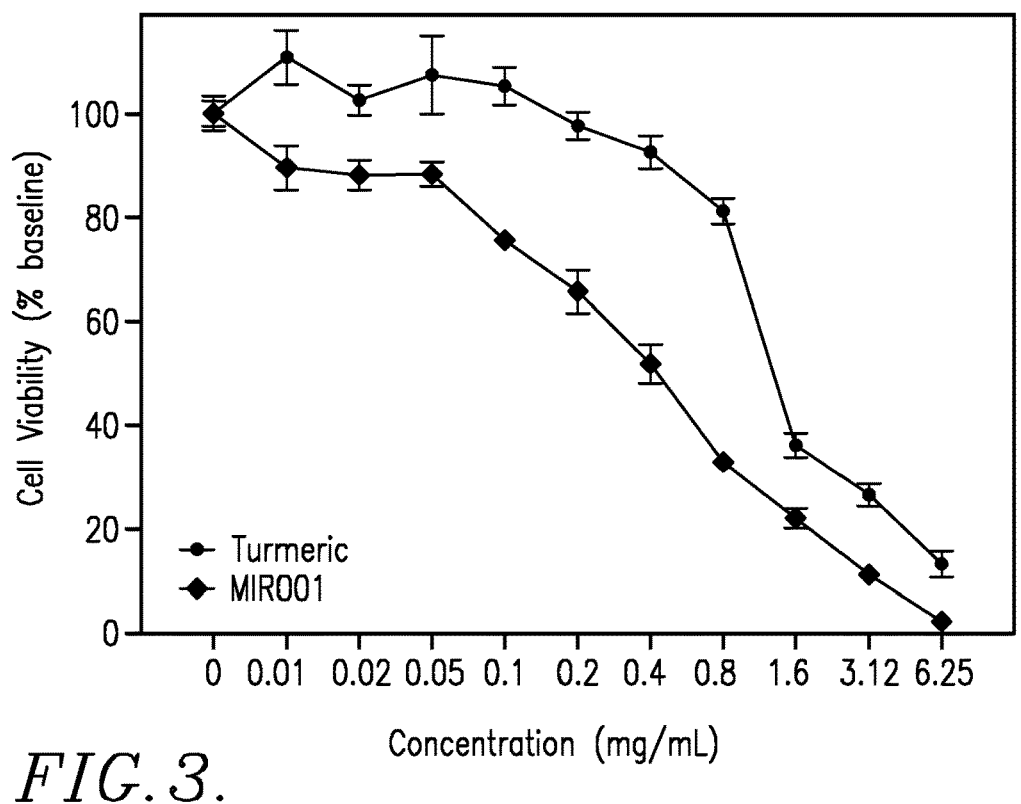
FIG. 3 is a graph illustrating the effect of MIR001 versus *Curcuma longa* alone, as set forth in the Example.
Figure 4:
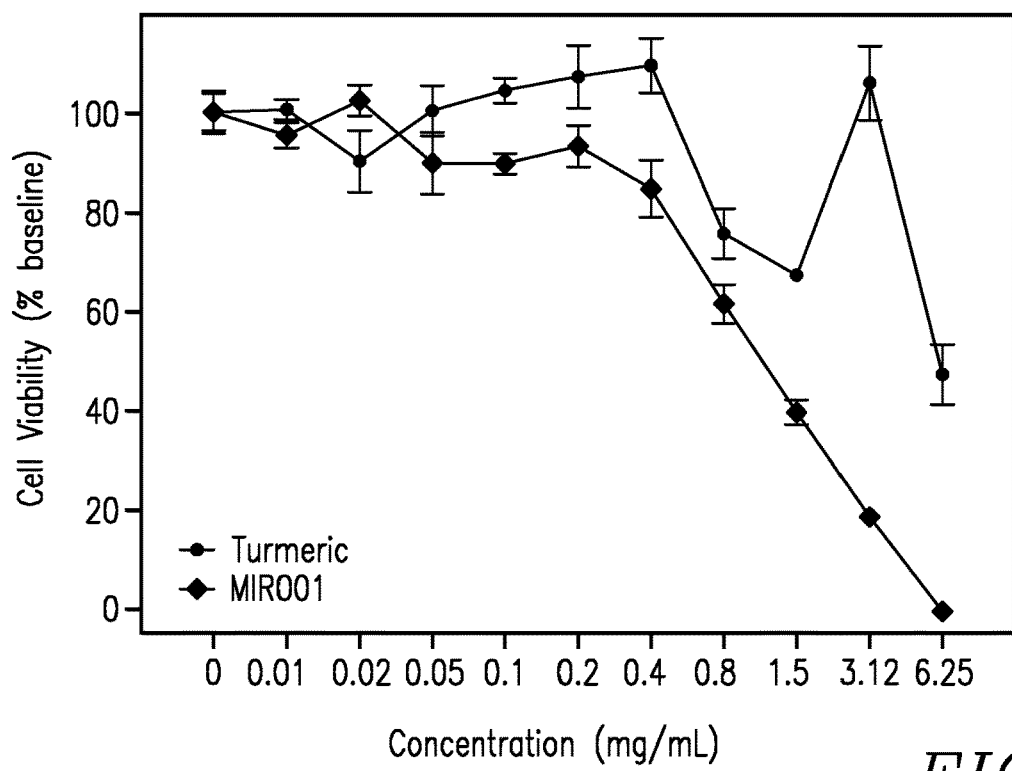
FIG. 4 is another graph illustrating the effect of MIR001 versus *Curcuma longa* alone, as set forth in the Example.
Figure 5:
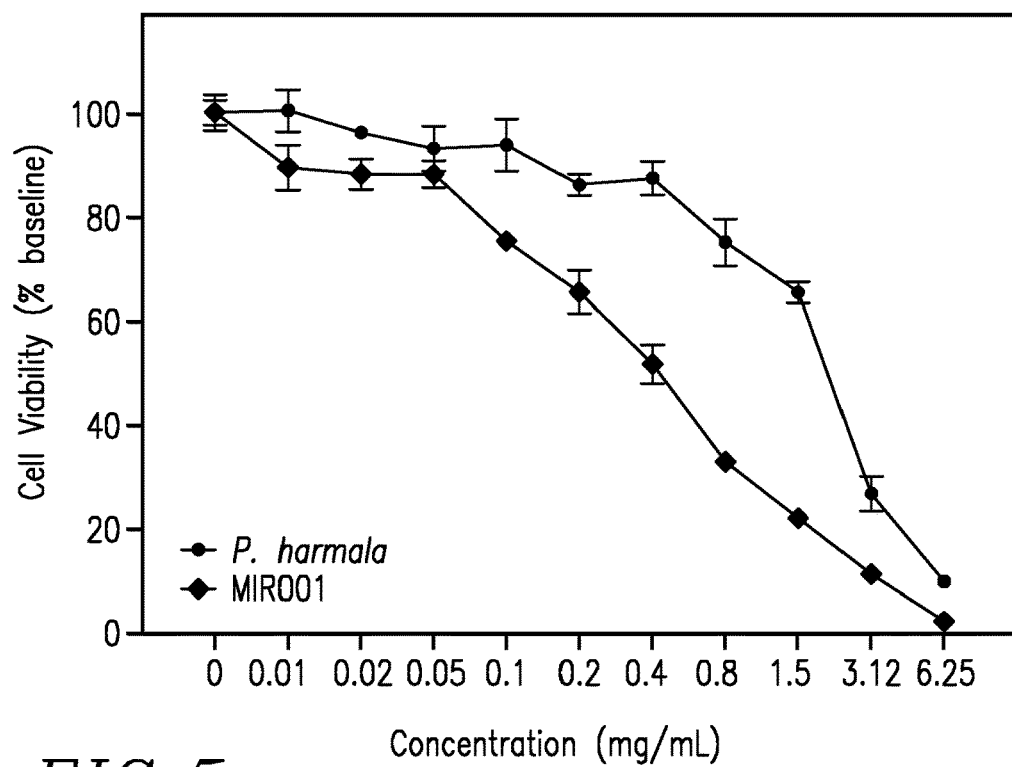
FIG. 5 is a graph illustrating the effect of MIR001 versus *Peganum harmala* alone, as set forth in the Example.
Figure 6:
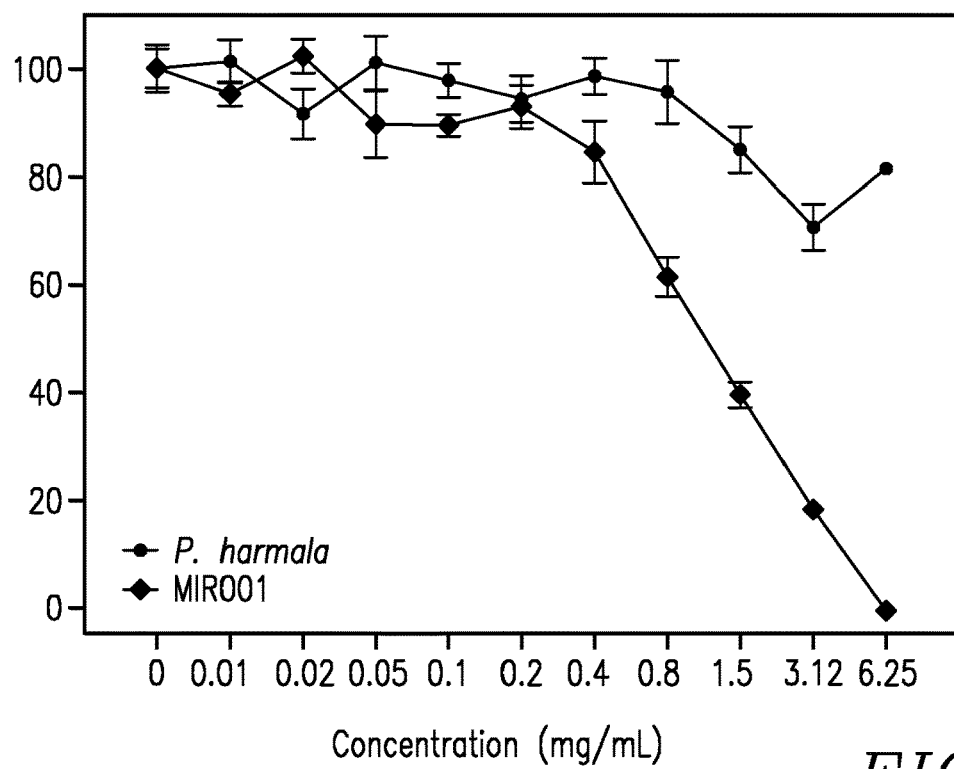
FIG. 6 is another graph illustrating the effect of MIR001 versus *Peganum harmala* alone, as set forth in the Example.

The effects of the individual plant extracts on ovarian spheroids was first tested. The results demonstrated that while each plant extract had some in vitro effect, the combination MIR001 was significantly more effective than each extract alone. These results are set forth in FIGS. 1-6. The *A. palaestinum* plant extract alone was the least effective (FIG. 1), while *C. longa* (turmeric; FIG. 3) and *P. Harmala* (FIG. 5) were more effective, at the highest concentrations tested. The same effect was noted when lung spheroids were exposed to MIR001; however, the differences were even greater. *A. palaestinum* alone failed to have even 20% effect in the lung spheroids, while MIR001 caused 80% effect at the same concentration (FIG. 2). Turmeric had greater variability between trials, but failed to reach more than 60% effect (FIG. 4). Likewise, *P. harmala* induced little effect alone (FIG. 6).

Figure 7:
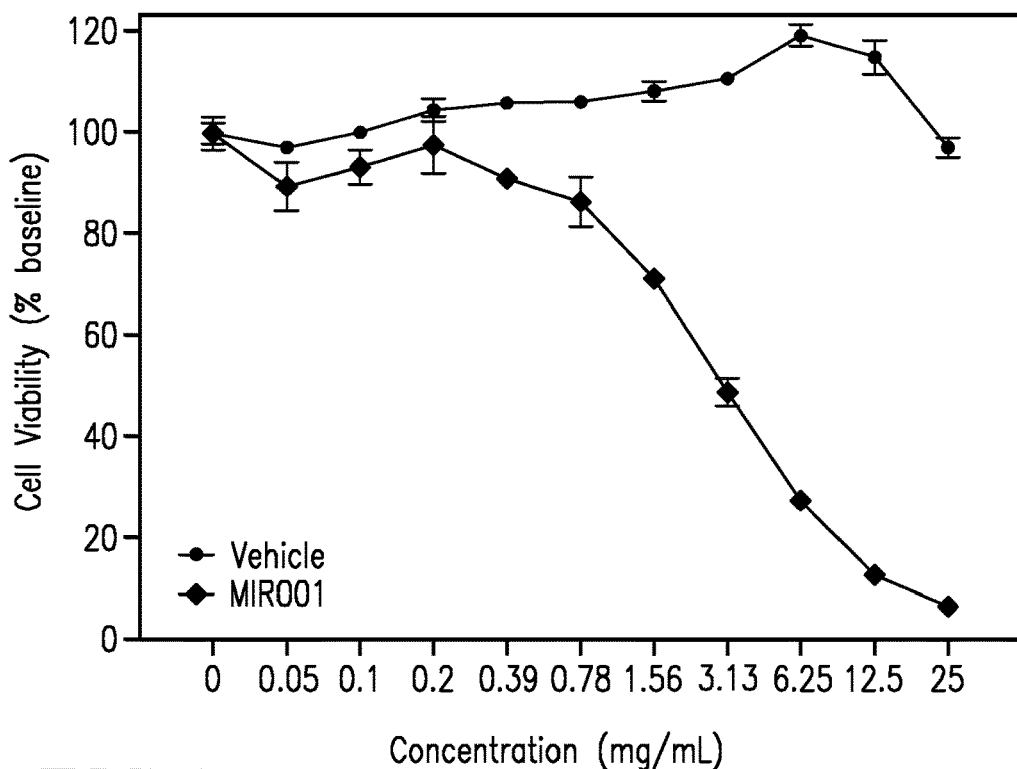
FIG. 7 is a graph illustrating the effect of MIR001 versus the RPMI/FBS test vehicle alone, as set forth in the Example.
Figure 8:
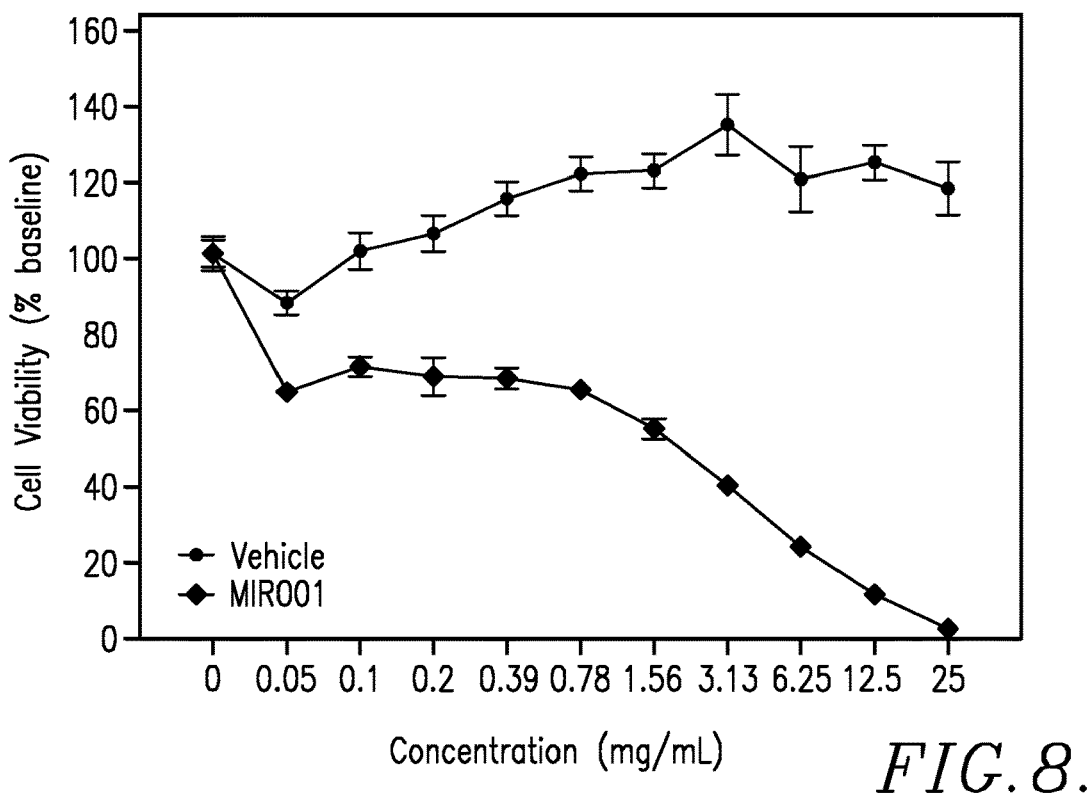
FIG. 8 is another graph illustrating the effect of MIR001 versus the RPMI/FBS test vehicle alone, as set forth in the Example.

The effects were specific to MIR001, because subsequent studies exposing the 3D spheroids to MIR001 versus the vehicle showed that the latter had no effect on ovarian spheroids (FIG. 7) or lung spheroids (FIG. 8).

These results demonstrate that the three-component composition MIR001 gave significant results as compared with the individual extracts.

We claim:

1. A nutritional supplement comprising turmeric, *Peganum harmala*, and *Arum palaestinum*, said turmeric present in an amount greater than either of the amounts of said

*Peganum harmala*, and said *Arum palaestinum*, wherein, said supplement is in the form of a capsule, gel, tablet or pill.

2. The supplement of claim 1, further comprising β-sitosterol.

3. The supplement of claim 1, further comprising a vanillin compound.

4. The supplement of claim 1, further comprising garlic.

5. The supplement of claim 1, further comprising Vitamin C.

6. The supplement of claim 1, said supplement further comprising garlic, β-sitosterol, and Vitamin C, said turmeric being present in an amount greater than any of *Peganum harmala, Arum palaestinum*, garlic, β-sitosterol, and Vitamin C.

7. The supplement of claim 1, said supplement having from about 8-15% by weight Vitamin C, from about 5-11% by weight garlic, from about 35-45% by weight vanillin, from about 5-11% by weight β-sitosterol, from about 12-20% by weight turmeric, from about 5-11% by weight *Peganum harmala*, and from about 5-11% *Arum palaestinum*.

8. The supplement of claim 7, said supplement having from about 9-11% by weight Vitamin C, from about 7-9% by weight garlic, from about 38-42% by weight vanillin, from about 7-9% by weight β-sitosterol, from about 14-17% by weight turmeric, from about 7-9% by weight *Peganum harmala*, and from about 7-9% *Arum palaestinum*.

9. The supplement of claim 1, said turmeric, *Peganum harmala*, and *Arum palaestinum* are food grade ingredients.

10. The supplement of claim 1, for for supporting or promoting of normal blood glucose levels.

11. The supplement of claim 1, for for supporting or promoting of prostate health.

12. The supplement of claim 1, for for supporting or promoting of normal cholesterol levels.

13. A supplement in in accordance with claim 1, for use in the support or promotion of normal cellular division.

14. The supplement of claim 1, wherein the amount of turmeric is 40-70% by weight and the amount of each of *Peganum harmala* and *Arum palaestinum* is 15-35% by weight, respectively.

* * * * *